(12) United States Patent
Kumar et al.

(10) Patent No.: US 11,234,690 B2
(45) Date of Patent: Feb. 1, 2022

(54) METHOD AND DEVICE FOR CLOSING A PORT SITE INCISION

(71) Applicant: Covidien LP, Mansfield, MA (US)

(72) Inventors: Neeraj Kumar, Noida (IN); Clifford L. Emmons, Dennis, MA (US)

(73) Assignee: Covidien LP, Mansfield, MA (US)

( * ) Notice: Subject to any disclaimer, the term of this patent is extended or adjusted under 35 U.S.C. 154(b) by 309 days.

(21) Appl. No.: 16/364,511

(22) Filed: Mar. 26, 2019

(65) Prior Publication Data

US 2019/0336122 A1 Nov. 7, 2019

Related U.S. Application Data (60) Provisional application No. 62/665,593, filed on May 2, 2018.

(51) Int. Cl.
*A61B 17/04* (2006.01)
*A61B 17/06* (2006.01)
*A61B 17/062* (2006.01)

(52) U.S. Cl.
CPC ........ *A61B 17/0482* (2013.01); *A61B 17/062* (2013.01); *A61B 17/06066* (2013.01); *A61B 2017/0608* (2013.01)

(58) Field of Classification Search
CPC .......... A61B 17/0482; A61B 17/06066; A61B 17/062; A61B 2017/0608;
(Continued)

(56) References Cited

U.S. PATENT DOCUMENTS 5,403,328 A * 4/1995 Shallman ........... A61B 17/0469
112/169
5,499,997 A 3/1996 Sharpe et al.
(Continued)

FOREIGN PATENT DOCUMENTS

EP 2305151 A1 4/2011
EP 2412317 A1 2/2012
(Continued)

OTHER PUBLICATIONS

European Search Report dated Oct. 7, 2019, issued in EP Appln. No. 19172126, seven pages.
(Continued)

*Primary Examiner* — Wade Miles
*Assistant Examiner* — Kankindi Rwego (57) ABSTRACT

A method and device are provided for closing a port site incision after a minimally invasive surgical procedure is performed. The closure device includes an access device and a suture needle. A body of the access device has a proximal portion and a distal portion and defines a channel that extends between the proximal and distal portions. A head of the access device is supported on the proximal portion of the body. The suture needle includes a shaft having a proximal portion and a distal portion, and a curved portion that extends from the distal portion of the shaft and includes a tip configured to penetrate tissue. The shaft extends through and is movable within a slot in the head to move the curved portion of the suture needle from an inactive position located within the channel to an active position positioned located externally of the channel.

20 Claims, 5 Drawing Sheets

(58) Field of Classification Search
CPC .... A61B 2017/06071; A61B 2017/06076; A61B 2017/06085; A61B 2017/0609; A61B 2017/09065; A61B 2017/061; A61B 2017/06104; A61B 17/06109; A61B 17/06114
USPC ........................................................ 606/148
See application file for complete search history.

(56) References Cited

U.S. PATENT DOCUMENTS

| | | |
|---|---|---|
| 5,507,757 A | 4/1996 | Sauer et al. |
| 5,507,758 A | 4/1996 | Thomason et al. |
| 5,527,343 A | 6/1996 | Bonutti |
| 5,653,716 A | 8/1997 | Malo et al. |
| 5,697,941 A | 12/1997 | Christy |
| 5,716,369 A | 2/1998 | Riza |
| 5,817,111 A | 10/1998 | Riza |
| 5,846,253 A | 12/1998 | Buelna et al. |
| 5,860,991 A | 1/1999 | Klein et al. |
| 5,868,762 A | 2/1999 | Cragg et al. |
| 5,899,911 A | 5/1999 | Carter |
| 5,902,311 A | 5/1999 | Andreas et al. |
| 5,948,001 A | 9/1999 | Larsen |
| 5,972,005 A | 10/1999 | Stalker et al. |
| 5,993,471 A | 11/1999 | Riza et al. |
| 5,993,474 A | 11/1999 | Ouchi |
| 6,022,360 A | 2/2000 | Reimels et al. |
| 6,036,699 A | 3/2000 | Andreas et al. |
| 6,059,800 A | 5/2000 | Hart et al. |
| 6,099,550 A | 8/2000 | Yoon |
| 6,110,184 A | 8/2000 | Weadock |
| 6,113,610 A | 9/2000 | Poncet |
| 6,136,010 A | 10/2000 | Modesitt et al. |
| 6,245,079 B1 | 6/2001 | Nobles et al. |
| 6,245,080 B1 | 6/2001 | Levinson |
| 6,296,648 B1 | 10/2001 | Boche et al. |
| 6,355,050 B1 | 3/2002 | Andreas et al. |
| 6,398,796 B2 | 6/2002 | Levinson |
| 6,491,707 B2 | 12/2002 | Makower et al. |
| 6,500,184 B1 | 12/2002 | Chan et al. |
| 6,517,553 B2 | 2/2003 | Klein et al. |
| 6,551,331 B2 | 4/2003 | Nobles et al. |
| 6,743,241 B2 | 6/2004 | Kerr |
| 6,770,084 B1 | 8/2004 | Bain et al. |
| 6,896,685 B1 | 5/2005 | Davenport |
| 6,939,357 B2 | 9/2005 | Navarro et al. |
| 7,004,952 B2 | 2/2006 | Nobles et al. |
| 7,048,749 B2 | 5/2006 | Kortenbach et al. |
| 7,090,686 B2 | 8/2006 | Nobles et al. |
| 7,291,155 B2 | 11/2007 | Batke et al. |
| 7,449,024 B2 | 11/2008 | Stafford |
| 7,462,188 B2 | 12/2008 | McIntosh |
| 7,601,161 B1 | 10/2009 | Nobles et al. |
| 7,722,629 B2 | 5/2010 | Chambers |
| 7,736,388 B2 | 6/2010 | Goldfarb et al. |
| 7,824,419 B2 | 11/2010 | Boraiah |
| 7,850,701 B2 | 12/2010 | Modesitt et al. |
| 8,038,687 B2 | 10/2011 | Pipenhagen et al. |
| 8,172,860 B2 | 5/2012 | Zung et al. |
| 8,211,122 B2 | 7/2012 | McIntosh |
| 8,317,679 B2 | 11/2012 | Surti |
| 8,348,962 B2 | 1/2013 | Nobles et al. |
| 9,675,342 B2 | 6/2017 | Prior et al. |
| 2002/0016614 A1 | 2/2002 | Klein et al. |
| 2002/0049453 A1 | 4/2002 | Nobles et al. |
| 2003/0009180 A1 | 1/2003 | Hinchliffe et al. |
| 2003/0028201 A1 | 2/2003 | Navarro et al. |
| 2004/0092964 A1 | 5/2004 | Modesitt et al. |
| 2004/0098047 A1 | 5/2004 | Frazier et al. |
| 2004/0186487 A1 | 9/2004 | Klein et al. |
| 2004/0199185 A1 | 10/2004 | Davignon |
| 2004/0225301 A1 | 11/2004 | Roop et al. |
| 2005/0119670 A1 | 6/2005 | Kerr |
| 2005/0212221 A1 | 9/2005 | Smith et al. |
| 2006/0195120 A1 | 8/2006 | Nobles et al. |
| 2007/0088247 A1 | 4/2007 | Bliweis et al. |
| 2007/0203507 A1 | 8/2007 | McLaughlin et al. |
| 2007/0250112 A1 | 10/2007 | Ravikumar et al. |
| 2008/0033459 A1 | 2/2008 | Shafi et al. |
| 2008/0097480 A1 | 4/2008 | Schorr et al. |
| 2008/0097481 A1 | 4/2008 | Schorr et al. |
| 2008/0255592 A1 | 10/2008 | Hsu et al. |
| 2010/0012152 A1 | 1/2010 | Hansen |
| 2010/0262166 A1 | 10/2010 | Boraiah et al. |
| 2011/0082475 A1 | 4/2011 | Smith |
| 2011/0237901 A1 | 9/2011 | Duke et al. |
| 2011/0270282 A1 | 11/2011 | Lemke |
| 2011/0313433 A1 | 12/2011 | Woodard, Jr. et al. |
| 2012/0010634 A1 | 1/2012 | Crabb et al. |
| 2012/0029532 A1 | 2/2012 | Hodgkinson et al. |
| 2012/0143221 A1 | 6/2012 | Weisel et al. |
| 2012/0191109 A1 | 7/2012 | Rockrohr |
| 2013/0079597 A1 | 3/2013 | Auerbach et al. |
| 2013/0165956 A1 | 6/2013 | Sherts et al. |
| 2016/0128681 A1 | 5/2016 | Hsu et al. |
| 2016/0345953 A1 | 12/2016 | Russell et al. |

FOREIGN PATENT DOCUMENTS

| | | |
|---|---|---|
| EP | 2547270 A1 | 1/2013 |
| WO | 9502998 A1 | 2/1995 |
| WO | 2006111955 A2 | 10/2006 |
| WO | 2011128392 A1 | 10/2011 |
| WO | 2012093094 A1 | 7/2012 |
| WO | 2013105993 A2 | 7/2013 |

OTHER PUBLICATIONS

European Office Action dated Oct. 6, 2020, issued in EP Appln. No. 19172126.

* cited by examiner

METHOD AND DEVICE FOR CLOSING A PORT SITE INCISION

CROSS-REFERENCE TO RELATED APPLICATION

This application claims the benefit of and priority to U.S. Provisional Patent Application No. 62/665,593 filed May 2, 2018, the entire disclosure of which is incorporated by reference herein.

BACKGROUND

1. Technical Description

The present disclosure is directed to a closure device for closing incisions, and more particularly, to a closure device for closing port site incisions after minimally invasive surgical procedures.

2. Background of Related Art

Minimally invasive surgical procedures including laparoscopic, endoscopic, and arthroscopic surgical procedures are performed through small incisions, or cannulas positioned through small incisions, in a body wall of a patient. These procedures impose less risk of infection and result in shortened hospital stays as compared to traditional open surgical procedures. After a minimally invasive surgical procedure is completed, port site incisions provided to access a surgical site must be closed or sutured. Current methods of closing port site incisions after minimally invasive surgical procedures are highly skill dependent and typically involve directing a curved needle through a small port and through fascial and muscular layers of tissue while attempting to avoid contact with internal body organs. This can be especially difficult after a laparoscopic procedure in the abdominal cavity.

A continuing need exists in the surgical arts for an improved closure device for sealing or closing a port site incision that is simple in construction and easy to use.

SUMMARY

One aspect of the disclosure is directed to a closure device for closing a port site incision that includes an access device and a suture needle. The access device includes a body defining a cutout and a head defining a slot. The body has a proximal portion and a distal portion and defines a channel that extends between the proximal and distal portions. The head is supported on the proximal portion of the body. The suture needle includes a shaft and a curved portion. The shaft has a proximal portion and a distal portion. The curved portion extends from the distal portion of the shaft and has a tip configured to penetrate tissue that extends in a direction towards the head of the access device. The proximal portion of the shaft extends through and is movable within the slot in the head to move the curved portion of the suture needle from an inactive position located within the channel to an active position located externally of the channel.

In embodiments, the suture needle has a J-shaped configuration.

In some embodiments, an actuator knob is secured to the shaft of the suture needle.

In certain embodiments, the actuator knob is slidably supported on the head of the access device and is movable to move the suture needle between the inactive position and the active position.

In embodiments, the tip of the suture needle extends in a direction towards the head of the access device.

In some embodiments, a suture is secured to the suture needle.

In certain embodiments, the suture needle includes an eyelet and the suture extends through the eyelet to couple the suture to the suture needle.

In embodiments, the head of the access device has a first diameter and the body of the access device has a second diameter, wherein the first diameter is greater than the second diameter.

In some embodiments, the head of the access device defines a suture hole and the suture extends from the eyelet of the suture needle through the suture hole.

In embodiments, the cutout in the body of the access device defines a vertical slot that is dimensioned to facilitate passage of the curved portion of the suture needle from within the channel into a body cavity.

In embodiments, the distal portion of the body of the access device includes a tapered end that is configured to facilitate passage of the body of the access device through the port site incision.

Another aspect of the disclosure is directed to a method for closing a port site incision in a body wall. The method includes inserting a body of an access device of a closure device through the port site incision in the body wall into a body cavity such that a head of the access device is positioned adjacent an outer surface of the body wall; moving a J-shaped needle having a tip configured to penetrate tissue from an inactive position located within a channel defined within the body of the closure device to an active position located within the body cavity externally of the channel; tilting the body within the incision in the body wall; withdrawing the body of the access device to move the head of the access device away from the outer surface of the body wall such that the tip of the J-shaped needle passes through the body wall to position a first end of a suture secured to the J-shaped needle adjacent one side of the incision near the outer surface of the body wall; and inserting the body of the access device through the incision in the body wall to reposition the body of the access device within the body cavity and reposition the head of the access device near the outer surface of the body wall.

In embodiments, moving the J-shaped needle from the inactive position to the active position includes sliding an actuator knob attached to a proximal portion of the J-shaped needle in relation to the head.

In embodiments, the method includes rotating the body of the access device within the incision to move the tip of the J-shaped needle from one side of the body to an opposite side of the body.

In some embodiments, the method includes moving the J-shaped needle from the active position back to the inactive position prior to rotating the body of the access device.

In embodiments, the method includes moving the J-shaped needle again from the inactive position located within the channel defined within the body of the access device to the active position located within the body cavity externally of the channel of the body of the access device.

In embodiments, the method includes tilting the body again within the incision in the body wall and withdrawing the body of the access device to move the head of the access device away from the outer surface of the body wall such that the tip of the J-shaped needle passes through the body wall again to position a second end of the suture adjacent a second side of the incision on the outer surface of the body wall.

In embodiments, the method includes grasping the first and second ends of the suture and applying tension to the suture to close the port site incision.

In embodiments, the body wall is the abdominal wall and the body cavity is the abdominal cavity.

BRIEF DESCRIPTION OF THE DRAWINGS

Various embodiments of the presently disclosed port site incision closure device are described herein below with reference to the drawings, wherein.

DETAILED DESCRIPTION OF EMBODIMENTS

The presently disclosed closure device will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel.

Figure 1:
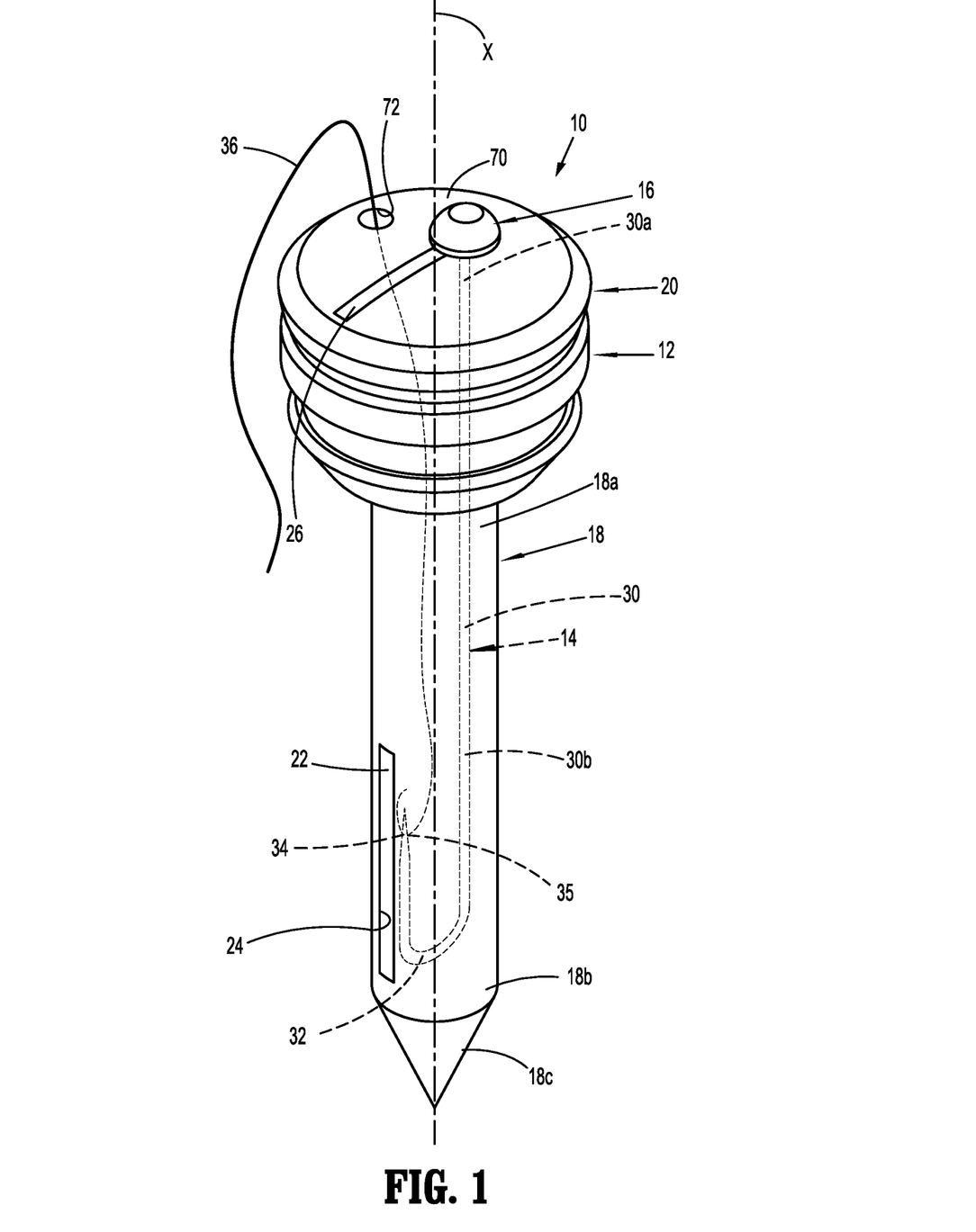
FIG. 1 is a side perspective view of an exemplary embodiment of the presently disclosed port site incision closure device ("closure device") with a suture needle in an inactive position and a suture attached to the suture needle and extending from an access device of the port site incision closure device.
Figure 2:
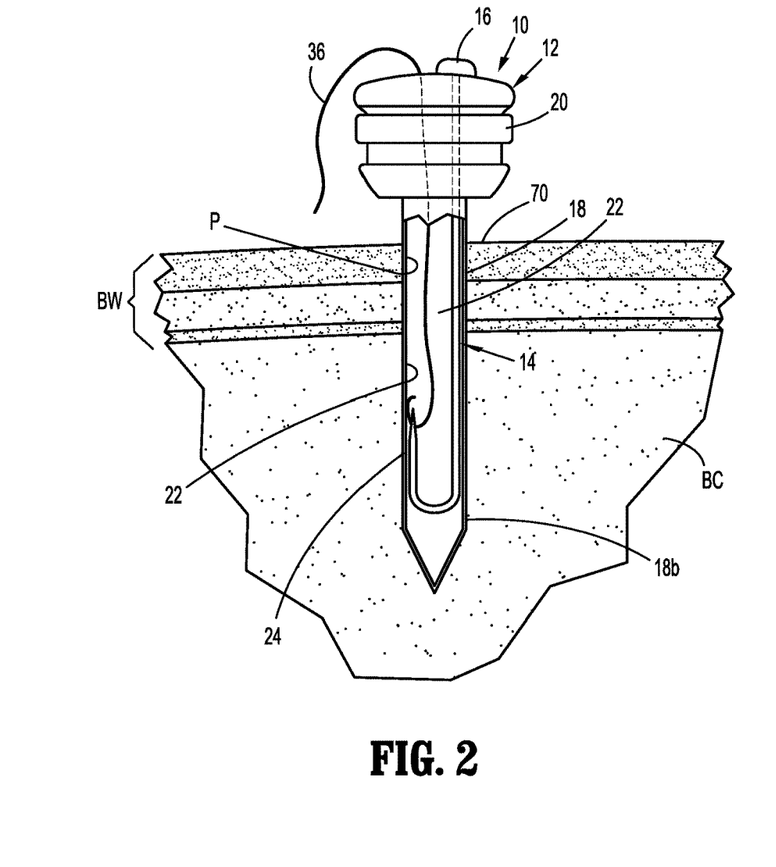
FIG. 2 is a side cross-sectional view of the closure device shown in FIG. 1 positioned through a port site incision with the suture needle in the inactive position, and the suture attached to the suture needle and extending from the access device.

FIGS. 1 and 2 illustrate an exemplary embodiment of the presently disclosed closure device which is shown generally as closure device 10. The closure device 10 includes an access device 12, a suture needle 14, and an actuation knob 16. The access device 12 includes a body 18 having a proximal portion 18a and a distal portion 18b, and a head 20 supported on the proximal portion 18a of the body 18. The body 18 and the head 20 of the access device 12 define a channel 22 (FIG. 2) that receives the suture needle 14 for movement between an inactive position (FIG. 2) and an active position (FIG. 3) as described in further detail below.

In embodiments, the body 18 defines a cutout or slot 24, e.g., a vertical oriented cutout or slot, and the head 20 defines a substantially horizontal cutout or slot 26. The cutout 24 is dimensioned to facilitate passage of a distal end of the suture needle 14 from within the channel 22 to a position externally of the channel 22. The slot 26 is dimensioned to facilitate passage of a proximal end of the suture needle 14 from within the channel 22 to a position adjacent an outer surface of the head 20. In some embodiments, the body 18 and the head 20 of the access device 12 are cylindrical and the head 20 has a diameter that is greater than a diameter of the body 18. The enlarged diameter of the head 20 of the access device 12 obstructs passage of the closure device 10 through a port site incision "P" (FIG. 2) into a body cavity "BC". In certain embodiments, the access device 12 may be in the form of an obturator wherein the distal portion 18b of the body 18 has a tapered end 18c to facilitate passage of the body 18 through the port site incision "P".

The suture needle 14 includes a needle shaft 30 and a curved portion 32. The needle shaft 30 has a proximal portion 30a and a distal portion 30b. The proximal portion 30a extends through and is movable laterally within the slot 26 in the head 20 of the access device 12 to facilitate movement of the suture needle 12 between the inactive position (FIG. 2) and the active position (FIG. 3) as described in further detail below. The curved portion 32 of the suture needle 12 includes a tip 34 that is configured to penetrate tissue. The tip 34 or a portion of the curved portion near the tip 34 defines an eyelet 35 through which a suture 36 can pass to secure the suture 36 to the suture needle 12. In embodiments, the curved portion 32 of the suture needle 12 is substantially U-shaped and the suture needle 12 is substantially J-shaped. In some embodiments, the tip 34 of the suture needle 12 is pointed towards the head 20 of the access device 12 and extends in a direction parallel to a longitudinal axis "X" (FIG. 1) of the access device 12. Alternately, other suture needle configurations are envisioned.

In some embodiments, the head 20 of the access device 12 defines a suture hole 72 (FIG. 1). The suture 36 extends from the eyelet 35 of the suture needle 12 through the channel 22 of the body 18 of the access device 12 and through the suture hole 72.

Figure 3:
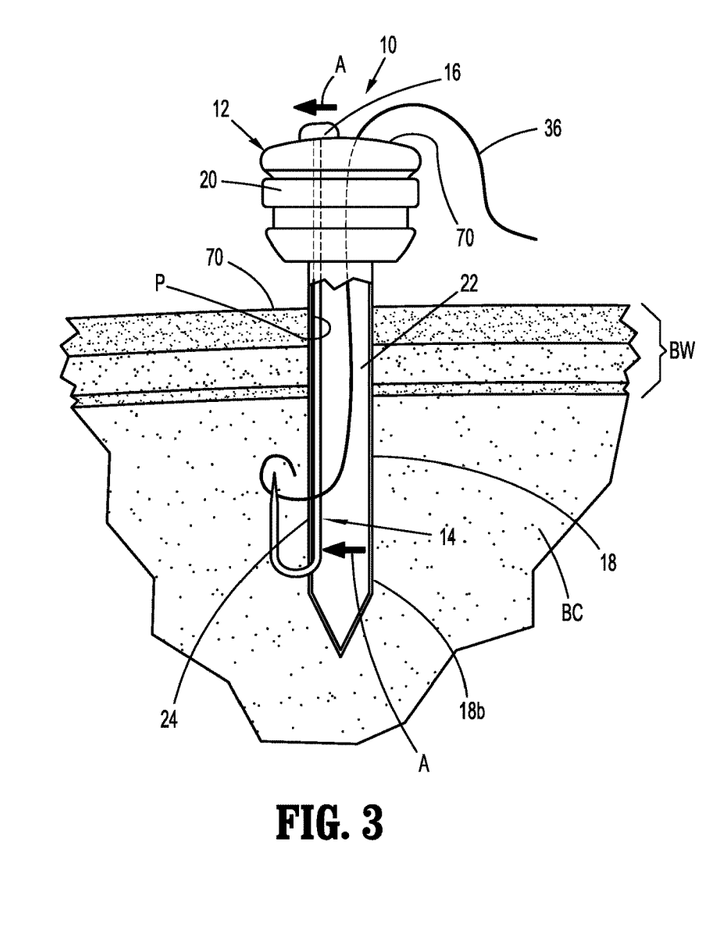
FIG. 3 is a side cross-sectional view of the closure device shown in FIG. 2 positioned through the port site incision with the suture needle in an active position and the suture attached to the suture needle and extending from the access device.

The actuation knob 16 is secured to the proximal portion 30a of the needle shaft 30 of the suture needle 12 and is movable in relation to the head 20 of the access device 12 to move the suture needle 12 between the inactive position (FIG. 2) and the active position (FIG. 3). In the inactive position, the curved portion 32 of the suture needle 14 is positioned within the channel 22 of the body 18 of the access device 12 such that the access device 12 can be safely inserted through the port site incision "P" without danger of the suture needle 14 inadvertently snagging and/or penetrating tissue. In the active position, the suture needle 14 is positioned externally of the channel 22 of the body 18 within a body cavity "BC" such that the body 18 of the access device 12 can be retracted or partially withdrawn from within the port site incision "P" to suture a body wall "BW", e.g., the abdominal wall, defining the incision "P" to close the incision "P". Because the tip 34 of the suture needle 12 is directed towards the head 20 of the access device 12 when the suture needle 12 is in the active position, the likelihood of inadvertent damage to internal organs within a body cavity "BC", e.g., the abdominal cavity, during manipulation of the closure device 10 is greatly reduced. Although the actuation knob 16 is shown as a button that is secured to the proximal portion 30a of the needle shaft 30, it is envisioned that other actuator configurations are envisioned.

FIGS. 2-9 illustrate use of the presently disclosed closure device 10 for closing a port site incision "P" in a body wall "BW" of a patient after a minimally invasive surgical procedure. Referring to FIGS. 2 and 3, after a minimally invasive surgical procedure is completed, or any time it becomes necessary to close an incision "P" in a body wall "BW" of a patient, the body 18 of the closure device 12 is inserted through the port site incision "P" in the body wall "BW" with a suture 36 secured to the suture needle 14 such that the distal portion 18b of the body 18 is positioned within the body cavity "BC" and the head 20 of the access device 12 is positioned near an outer surface 70 of the body wall "BW". After the access device 12 is properly positioned within the incision "P", the suture needle 14 is moved from the inactive position (FIG. 2) to the active position (FIG. 3) in the direction indicated by arrows "A" by sliding the actuation knob 16 in relation to the head 20 of the access device 12 along the horizontal slot 26. As the suture needle 14 moves towards the active position, the curved portion 32 of the suture needle 14 moves through the cutout 24 of the body 18 and passes from the channel 22 into the body cavity "BC". As shown, in the active position, the tip 34 of the suture needle 12 is directed towards the incision "P" and the head 20 of the access device 12.

Figure 4:
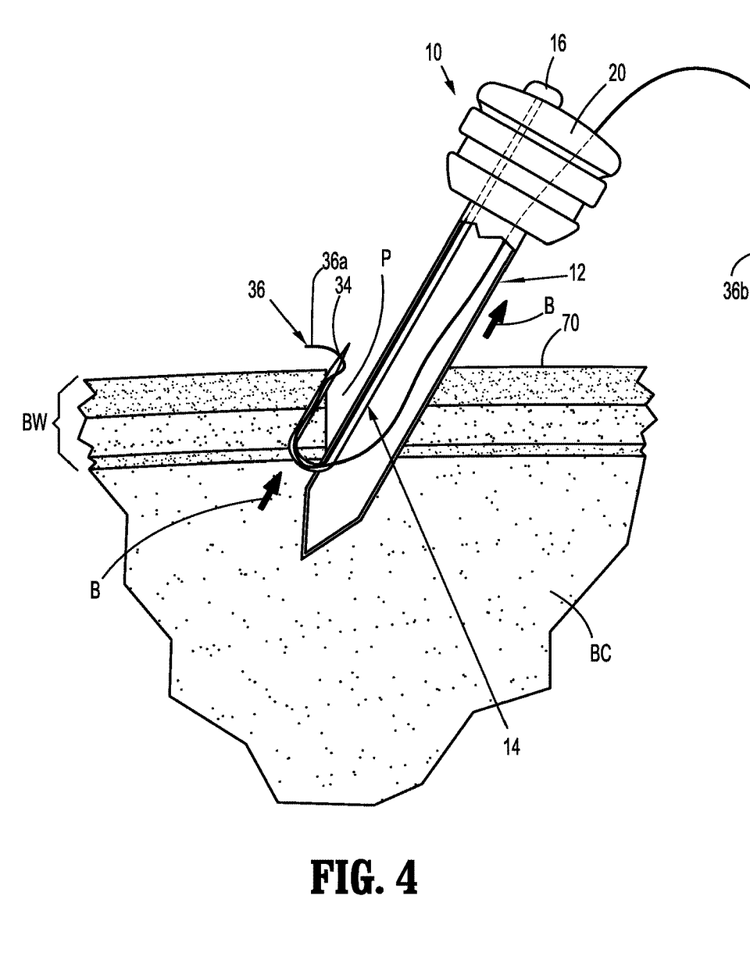
FIG. 4 is a side cross-sectional view of the closure device shown in FIG. 3 positioned through the port site incision with the suture needle in an active position and the closure device tilted and retracted to position the suture needle through tissue on one side of the port site incision to position a first end of the suture externally of tissue.

Referring to FIG. 4, after the suture needle 14 is in the active position, the access device 12 can be tilted and partially withdrawn from within the incision "P" in the direction indicated by arrows "B" to move the head 20 of the access device 12 away from the outer surface 70 of the body wall "BW" such that the tip 34 of the suture needle 14 passes through the body wall "BW" to position a first end 36a of the suture 36 adjacent one side of the incision "P" near the outer surface 70 of the body wall "BW". When the first end 36a of the suture 36 is accessible to a clinician, the clinician grasps and holds the first end 36a of the suture 36.

Figure 5:
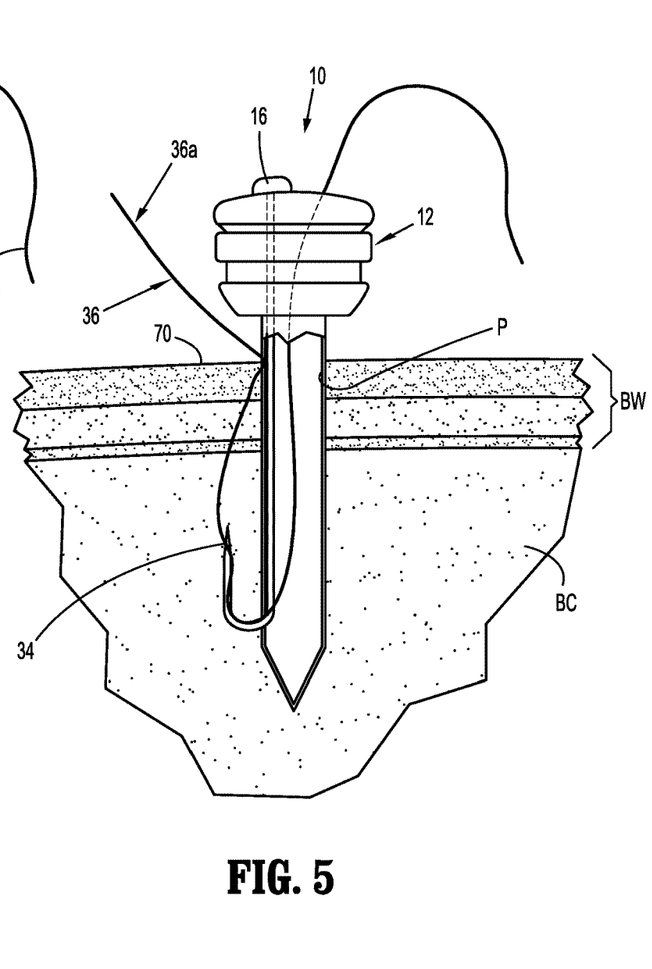
FIG. 5 is a side cross-sectional view of the closure device shown in FIG. 4 positioned through the port site incision with the suture needle in an active position and the closure device returned to a non-tilted position advanced position to withdraw the suture needle from the tissue.

Referring to FIG. 5, after the clinician has a firm grasp on the first end 36a of the suture 36, the access device 12 is further inserted through the incision "P" in the body wall "BW" to reposition the body 18 within the body cavity "BC" and reposition the head 20 of the access device 12 adjacent or nearer to the outer surface 70 of the body wall "BW".

Figure 6:
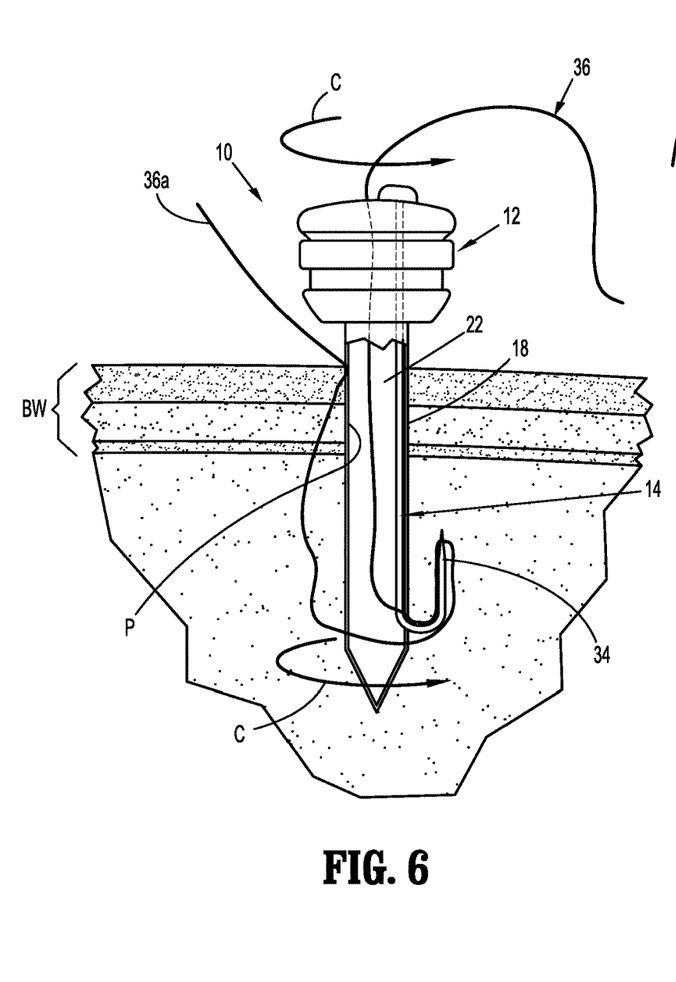
FIG. 6 is a side cross-sectional view of the closure device shown in FIG. 5 positioned through the port site incision with the suture needle in an active position and the closure device rotated about one hundred eighty degrees (180°)

Referring to FIG. 6, after the body 18 of the access device 12 is repositioned within the body cavity "BC", the access device 12 can be rotated in the direction indicated by arrows "C" within the incision "P" to reposition the tip 34 of the suture needle 14 beneath an opposite side of the incision "P". Although not shown, it is envisioned that prior to rotating the access device 12, the suture needle 14 can be returned to its inactive position by once again moving the actuation button 16 along the slot 26 to move the suture needle 14 back into the channel 22 of the body 18 of the access device 12. In either method of use, the suture needle 12 should be moved to the active position (FIG. 6) after the access device 12 is rotated to the position shown in FIG. 6.

Figure 7:
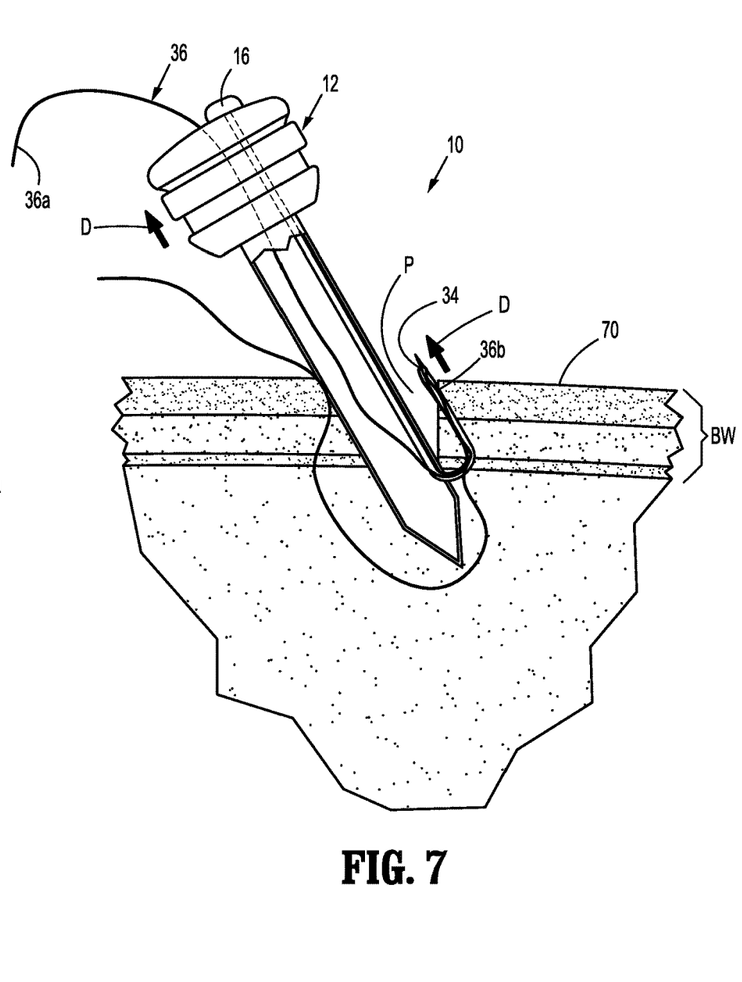
FIG. 7 is a side cross-sectional view of the closure device shown in FIG. 6 positioned through the port site incision with the suture needle in an active position and the closure device tilted in an opposite direction and retracted to position the suture needle through tissue on the other side of the port site incision to position a second end of the suture externally of tissue.

Referring to FIG. 7, after the access device 12 is rotated to the position shown in FIG. 6, the access device 12 can be tilted in an opposite direction and partially withdrawn from within the incision "P" in the direction indicated by arrows "D" to move the head 20 of the access device 12 away from the outer surface 70 of the body wall "BW" such that the tip 34 of the suture needle 12 passes through the body wall "BW" adjacent an opposite side of the incision "P" to position a second end 36b of the suture 36 adjacent the other side of the incision "P" near the outer surface 70 of the body wall "BW". When the second end 36b of the suture 36 is accessible to a clinician, the clinician grasps and holds the second end of the suture 36.

Figure 8:
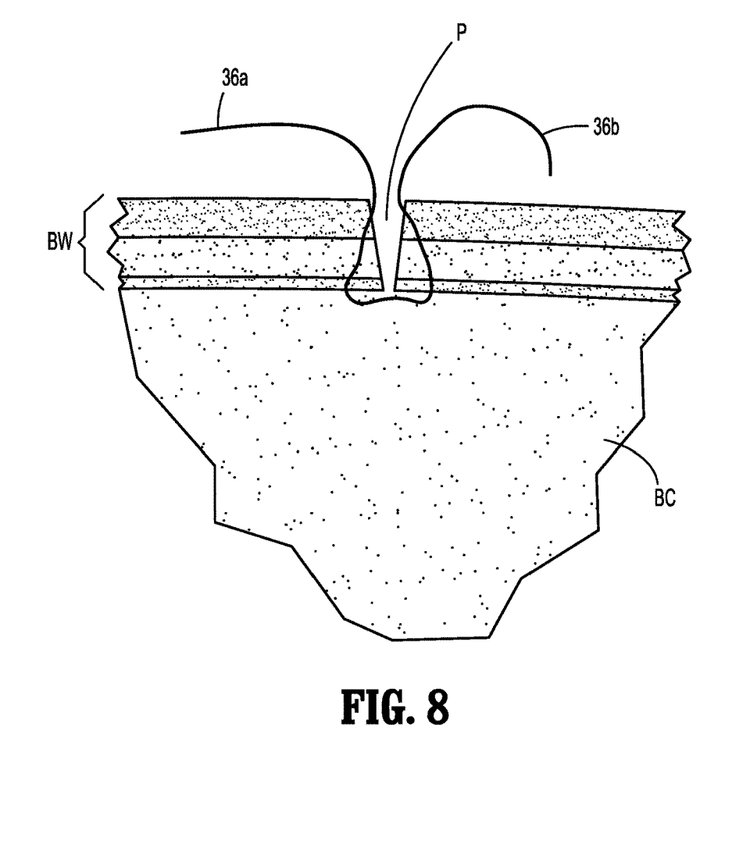
FIG. 8 is a side cross-sectional view of the port site incision defined by the tissue with opposite ends of the suture positioned on opposite sides of the incision.
Figure 9:
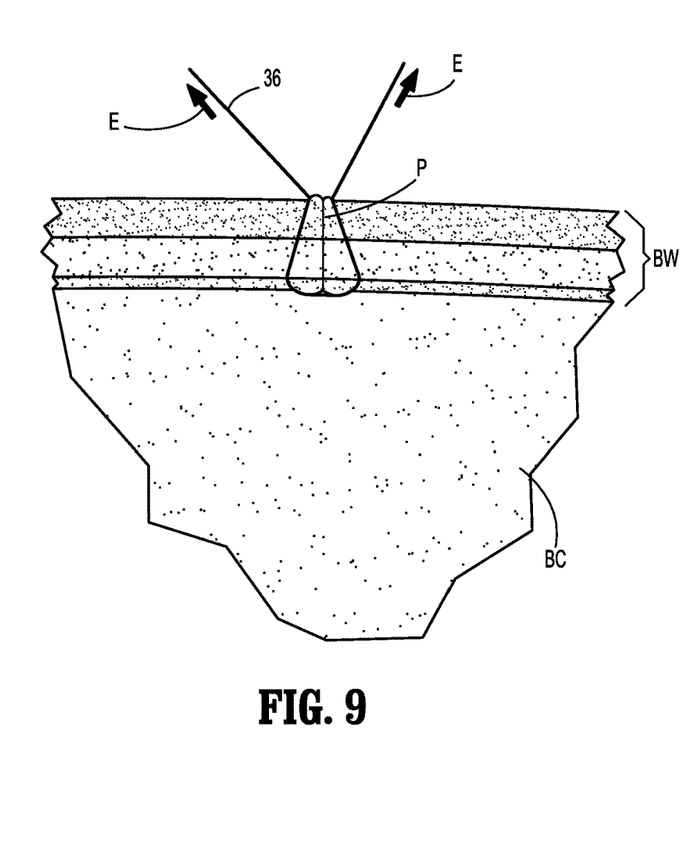
FIG. 9 is a side cross-sectional view of the port site incision defined by the tissue with opposite ends of the suture positioned on opposite sides of the port site incision and the suture tensed to close the incision.

Referring to FIGS. 8 and 9, after the clinician has a grasp on both ends 36a, 36b of the suture 36, the closure device 10 can be withdrawn from the incision "P" and properly disposed of in a customary manner. Thereafter, the clinician can apply tension to the ends 36a, 36b of the suture in the direction indicated by arrows "E" to close the incision "P".

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A closure device for closing a port site incision, the closure device comprising:

an access device defining a longitudinal axis and including a body defining a cutout and a head defining a slot, the body having a proximal portion and a distal portion and defining a channel that extends between the proximal and distal portions, the head being supported on the proximal portion of the body; and a suture needle including a shaft and a curved portion, the shaft having a proximal portion and a distal portion, the curved portion extending from the distal portion of the shaft and having a tip configured to penetrate tissue, the tip extending in a direction towards the head of the access device, wherein the proximal portion of the shaft extends through and is movable laterally within the slot in the head to move the curved portion of the suture needle from an inactive position located within the channel through the cutout to an active position positioned located externally of the channel.

2. The closure device of claim 1, wherein the head of the access device has a first diameter and the body of the access device has a second diameter, the first diameter being greater than the second diameter.

3. The closure device of claim 1, wherein the cutout in the body of the access device defines a vertical slot that is dimensioned to facilitate passage of the curved portion of the suture needle from within the channel into a body cavity.

4. The closure device of claim 1, wherein the distal portion of the body of the access device includes a tapered end, the tapered end facilitating passage of the body of the access device through the port site incision.

5. The closure device of claim 1, further including an actuator knob secured to the shaft of the suture needle.

6. The closure device of claim 5, wherein the actuator knob is slidably supported on the head of the access device and is movable laterally along the slot to move the suture needle between the inactive position and the active position.

7. The closure device of claim 1, wherein the suture needle has a J-shaped configuration.

8. The closure device of claim 7, wherein the tip of the suture needle extends towards the head of the access device.

9. The closure device of claim 8, further including a suture secured to the suture needle.

10. The closure device of claim 9, wherein the suture needle includes an eye, the suture extending through the eye to couple the suture to the suture needle.

11. The closure device of claim 10, wherein the head of the access device defines a suture hole, the suture extending from the eye of the suture needle through the suture hole.

12. A closure device for closing a port site incision, the closure device comprising:

an access device defining a longitudinal axis and including a body defining a vertical cutout and a head defining a horizontal slot, the body having a proximal portion and a distal portion and defining a channel that extends between the proximal and distal portions, the head being supported on the proximal portion of the body; and a suture needle including a shaft and a curved portion, the shaft having a proximal portion and a distal portion, the curved portion extending from the distal portion of the shaft and having a tip configured to penetrate tissue, the tip extending in a direction towards the head of the access device, wherein the proximal portion of the shaft extends through and is movable laterally within the horizontal slot in the head to move the curved portion of the suture needle through the vertical cutout from an inactive position located within the channel to an active position positioned located externally of the channel.

13. The closure device of claim 12, wherein the head of the access device has a first diameter, and the body of the access device has a second diameter, the first diameter being greater than the second diameter.

14. The closure device of claim 12, wherein the distal portion of the body of the access device includes a tapered end, the tapered end facilitating passage of the body of the access device through the port site incision.

15. The closure device of claim 12, further including an actuator knob secured to the shaft of the suture needle.

16. The closure device of claim 15, wherein the actuator knob is slidably supported on the head of the access device and is movable laterally along the slot to move the suture needle through the vertical cutout between the inactive position and the active position.

17. The closure device of claim 12, wherein the suture needle has a J-shaped configuration.

18. The closure device of claim 17, wherein the tip of the suture needle extends towards the head of the access device.

19. The closure device of claim 18, further including a suture, the suture needle having an eye and the suture extending through the eye to couple the suture to the suture needle.

20. The closure device of claim 19, wherein the head of the access device defines a suture hole, the suture extending from the eye of the suture needle through the suture hole.

* * * * *